US012788702B2

(12) United States Patent
Leal et al.

(10) Patent No.: US 12,788,702 B2
(45) Date of Patent: Nov. 10, 2026

(54) HAIR SHAMPOO WITH NATURAL OIL

(71) Applicants: Dow Global Technologies LLC, Midland, MI (US); Rohm and Haas Company, Collegeville, PA (US); Dow Silicones Corporation, Midland, MI (US)

(72) Inventors: Lyndsay M. Leal, Spring City, PA (US); Benjamin Reiner, Collegeville, PA (US); Nisaraporn Suthiwangcharoen, Midland, MI (US); Binghe Gu, Midland, MI (US)

(73) Assignees: Dow Global Technologies LLC, Midland, MI (US); Rohm and Haas Company, Collegeville, PA (US); Dow Silicones Corporation, Midland, MI (US)

( * ) Notice: Subject to any disclaimer, the term of this patent is extended or adjusted under 35 U.S.C. 154(b) by 186 days.

(21) Appl. No.: 18/847,697

(22) PCT Filed: Mar. 20, 2023

(86) PCT No.: PCT/US2023/015607
§ 371 (c)(1),
(2) Date: Sep. 17, 2024

(87) PCT Pub. No.: WO2023/183214
PCT Pub. Date: Sep. 28, 2023

(65) Prior Publication Data

US 2025/0195385 A1 Jun. 19, 2025

Related U.S. Application Data

(60) Provisional application No. 63/322,238, filed on Mar. 22, 2022.

(51) Int. Cl.

| | |
|---|---|
| ***A61K 8/73*** | (2006.01) |
| ***A61K 8/42*** | (2006.01) |
| ***A61K 8/44*** | (2006.01) |
| ***A61K 8/46*** | (2006.01) |
| ***A61K 8/86*** | (2006.01) |
| ***A61Q 5/02*** | (2006.01) |

(52) U.S. Cl.
CPC .................. *A61K 8/73* (2013.01); *A61K 8/42* (2013.01); *A61K 8/44* (2013.01); *A61K 8/463* (2013.01); *A61K 8/86* (2013.01); *A61Q 5/02* (2013.01); *A61K 2800/34* (2013.01)

(58) Field of Classification Search
None
See application file for complete search history.

(56) References Cited

U.S. PATENT DOCUMENTS

| | | | | |
|---|---|---|---|---|
| 8,076,279 | B2 | 12/2011 | Brand et al. | |
| 2006/0163149 | A1 | 7/2006 | Wadstrom et al. | |
| 2010/0093584 | A1* | 4/2010 | Brand | A61K 8/736 510/159 |
| 2022/0019469 | A1 | 1/2022 | Ji et al. | |
| 2022/0027984 | A1 | 1/2022 | Charton et al. | |

FOREIGN PATENT DOCUMENTS

| | | |
|---|---|---|
| WO | 2021194804 | 9/2021 |
| WO | 2021194807 | 9/2021 |
| WO | 2021194809 | 9/2021 |
| WO | 2022203866 | 9/2022 |
| WO | 2022240664 | 11/2022 |

* cited by examiner

*Primary Examiner* — Brian J Davis
(74) *Attorney, Agent, or Firm* — Thomas S. Deibert

(57) ABSTRACT

A hair care formulation is provided, comprising: a dermatologically acceptable vehicle; a surfactant; a dermatologically acceptable oil; and a deposition aid polymer, wherein the deposition aid polymer is a cationic dextran polymer, comprising a dextran base polymer functionalized with quaternary ammonium groups; wherein the dextran base polymer has a weight average molecular weight of 50,000 to 3,000,000 Daltons; wherein the quaternary ammonium groups include a group of formula (II) (II); and a group of formula (III) (III); wherein is a pendent oxygen on the dextran base polymer; wherein X is a divalent linking group; wherein each R2 is independently selected from a C1-4 alkyl group; wherein each R3 is independently selected from a C1-4 alkyl group; and wherein each R4 is independently selected from a linear or branched C12 alkyl group; wherein the deposition aid polymer has a degree of substitution, DS(II), of formula (II) moieties of 0.01 to 0.2 and a degree of substitution, DS(III), of formula (III) moieties of >0 to <0.02.

(II)

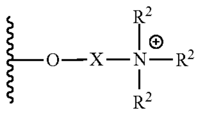

(III)

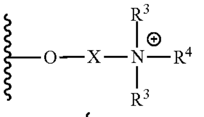

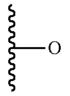

9 Claims, No Drawings

HAIR SHAMPOO WITH NATURAL OIL

The present invention relates to a hair care formulation. In particular, the present invention relates to a hair care formulation containing: a dermatologically acceptable vehicle; a hair cleaning surfactant; a dermatologically acceptable oil; and a deposition aid polymer, wherein the deposition aid polymer is a cationic dextran polymer, comprising a dextran base polymer functionalized with quaternary ammonium groups; wherein the dextran base polymer has a weight average molecular weight of 50,000 to 3,000,000 Daltons; wherein the quaternary ammonium groups include (i) a quaternary ammonium group of formula (II) bound to a pendent oxygen on the dextran base polymer

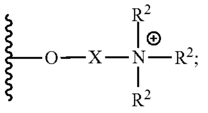

(II)

(ii) a quaternary ammonium group of formula (III) bound to a pendent oxygen on the dextran base polymer

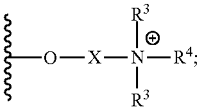

(III)

wherein

is a pendent oxygen on the dextran base polymer; wherein X is a divalent linking group; wherein each $R^2$ is independently selected from a $C_{1-4}$ alkyl group; wherein each $R^3$ is independently selected from a $C_{1-4}$ alkyl group; and wherein each $R^4$ is independently selected from a linear or branched $C_{12}$ alkyl group; wherein the deposition aid polymer has a degree of substitution, $DS_{(II)}$, of formula (II) moieties of 0.01 to 0.2 and a degree of substitution, $DS_{(III)}$, of formula (III) moieties of >0 to <0.02.

Deposition of oil is of particular interest for various personal care compositions. In particular, there is interest for hair cleansers (e.g., shampoo, shampoo conditioners) that provide moisturizing/conditioning benefits in addition to cleaning benefits.

Hair cleaning has become an ubiquitous component of personal hygiene. Cleaning of the hair facilitates the removal of dirt, germs and other things that are perceived as harmful to the hair or the individual. Cleaning formulations typically include a surfactant to promote the removal of materials deposited on the hair. Unfortunately, the cleaning formulations remove both undesirable and desirable materials from hair. For example, cleaning formulations frequently remove oils from hair, which is undesirable because oils operate to protect hair from loss of moisture. Removal of too much oil from hair may leave the hair vulnerable to becoming dry and damaged. One solution to this concern is the selection of mild surfactants.

Another approach is to incorporate additives that help replace the oils removed through deposition; however, this approach has proven difficult in implementation, particularly in rinse off applications.

In U.S. Pat. No. 7,067,499, Erazo-Majewicz, et al disclose personal care and household care product composition comprising at least one cationic polygalactomannan or a derivative of cationic polygalactomannans wherein the derivative moiety on the cationic derivatized polygalactomannan is selected from the group consisting of alkyl, hydroxyalkyl, alkylhydroxyalkyl, and carboxymethyl wherein the alkyl has a carbon chain containing from 1 to 22 carbons and the hydroxyalkyl is selected from the group consisting of hydroxyethyl, hydroxypropyl, and hydroxybutyl, wherein the at least one cationic polygalactomannan or derivative of cationic polygalactomannans have a mean average molecular weight (Mw) having a lower limit of 5,000 and an upper limit of 200,000 and having a light transmittance in a 10% aqueous solution of greater than 80% at a light wavelength of 600 nm and a protein content of less than 1.0% by weight of polysaccharide, and aldehyde functionality content of at least 0.01 meg/gram.

While conventionally used deposition aids such as soluble cationic modified celluloses (e.g., polyquaternium-10), guar hydroxypropyltrimonium chloride and other cationic polymers (e.g., polyquaternium-6, polyquaternium-7) provide a certain level of deposition in personal care cleansers; they nevertheless exhibit low efficiency necessitating a relatively high incorporation of the active into the personal care cleanser formulation to facilitate desired results. Such high active (e.g., oil) levels, however, detrimentally effect the foam/lathery in use consumer feel of the formulation and cost.

Accordingly, there remains a need for deposition aids that facilitate enhanced efficiency of oil deposition from hair care formulations, in particular from hair cleaning surfactant containing hair care formulations.

The present invention provides a hair care formulation, comprising: a dermatologically acceptable vehicle; a hair cleaning surfactant; a dermatologically acceptable oil; and a deposition aid polymer, wherein the deposition aid polymer is a cationic dextran polymer, comprising a dextran base polymer functionalized with quaternary ammonium groups; wherein the dextran base polymer has a weight average molecular weight of 50,000 to 3,000,000 Daltons; wherein the quaternary ammonium groups include (i) a quaternary ammonium group of formula (II) bound to a pendent oxygen on the dextran base polymer

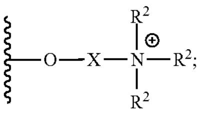

(II)

and (ii) a quaternary ammonium group of formula (III) bound to a pendent oxygen on the dextran base polymer (III)

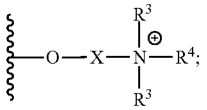

wherein

is a pendent oxygen on the dextran base polymer; wherein X is a divalent linking group; wherein each $R^2$ is independently selected from a $C_{1-4}$ alkyl group; wherein each $R^3$ is independently selected from a $C_{1-4}$ alkyl group; and wherein each $R^4$ is independently selected from a linear or branched $C_{12}$ alkyl group; wherein the deposition aid polymer has a degree of substitution, $DS_{(II)}$, of formula (II) moieties of 0.01 to 0.2 and a degree of substitution, $DS_{(III)}$, of formula (III) moieties of >0 to <0.02.

The present invention provides a hair care formulation, comprising: a dermatologically acceptable vehicle; a hair cleaning surfactant; a dermatologically acceptable oil; and a deposition aid polymer, wherein the deposition aid polymer is a cationic dextran polymer, comprising a dextran base polymer functionalized with quaternary ammonium groups; wherein the dextran base polymer has a weight average molecular weight of 50,000 to 3,000,000 Daltons; wherein the quaternary ammonium groups include (i) a quaternary ammonium group of formula (II) bound to a pendent oxygen on the dextran base polymer; and (ii) a quaternary ammonium group of formula (III) bound to a pendent oxygen on the dextran base polymer; wherein

is a pendent oxygen on the dextran base polymer; wherein X is a divalent linking group; wherein each $R^2$ is independently selected from a $C_{1-4}$ alkyl group; wherein each $R^3$ is independently selected from a $C_{1-4}$ alkyl group; and wherein each $R^4$ is independently selected from a linear or branched $C_{12}$ alkyl group; wherein the deposition aid polymer has a degree of substitution, $DS_{(II)}$, of formula (II) moieties of 0.01 to 0.2 and a degree of substitution, $DS_{(III)}$, of formula (III) moieties of >0 to <0.02; and wherein the hair care formulation contains less than 0.1 wt %, based on weight of the hair care formulation, of silicon containing molecules.

The present invention provides a hair care formulation, comprising: a dermatologically acceptable vehicle; a hair cleaning surfactant including a sodium lauryl ether sulfate; a dermatologically acceptable oil; and a deposition aid polymer, wherein the deposition aid polymer is a cationic dextran polymer, comprising a dextran base polymer functionalized with quaternary ammonium groups; wherein the dextran base polymer has a weight average molecular weight of 50,000 to 3,000,000 Daltons; wherein the quaternary ammonium groups include (i) a quaternary ammonium group of formula (II) bound to a pendent oxygen on the dextran base polymer; and (ii) a quaternary ammonium group of formula (III) bound to a pendent oxygen on the dextran base polymer; wherein

is a pendent oxygen on the dextran base polymer; wherein X is a divalent linking group; wherein each $R^2$ is independently selected from a $C_{1-4}$ alkyl group; wherein each $R^3$ is independently selected from a $C_{1-4}$ alkyl group; and wherein each $R^4$ is independently selected from a linear or branched $C_{12}$ alkyl group; wherein the deposition aid polymer has a degree of substitution, $DS_{(II)}$, of formula (II) moieties of 0.01 to 0.2 and a degree of substitution, $DS_{(III)}$, of formula (III) moieties of >0 to <0.02; and wherein the hair care formulation contains less than 0.1 wt %, based on weight of the hair care formulation, of silicon containing molecules.

The present invention provides a method of depositing oil on to mammalian hair, comprising: selecting a hair care formulation of the present invention; and applying the hair care formulation to mammalian hair; wherein the deposition aid polymer enhances the deposition of the dermatologically acceptable oil from the hair care formulation onto the mammalian hair relative to an otherwise identical formulation without the deposition aid polymer.

DETAILED DESCRIPTION

We have surprisingly found that oil deposition from hair care formulations containing a hair cleaning surfactant can be enhanced through incorporation of a deposition aid polymer, wherein the deposition aid polymer is a cationic dextran polymer, comprising a dextran base polymer functionalized with quaternary ammonium groups; wherein the dextran base polymer has a weight average molecular weight of 50,000 to 3,000,000 Daltons; wherein the quaternary ammonium groups include (i) a quaternary ammonium group of formula (II) bound to a pendent oxygen on the dextran base polymer (II)

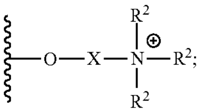

and (ii) a quaternary ammonium group of formula (III) bound to a pendent oxygen on the dextran base polymer (III)

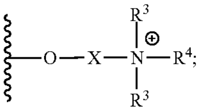

wherein

is a pendent oxygen on the dextran base polymer; wherein X is a divalent linking group; wherein each $R^2$ is independently selected from a $C_{1-4}$ alkyl group; wherein each $R^3$ is independently selected from a $C_{1-4}$ alkyl group; and wherein each $R^4$ is independently selected from a linear or branched $C_{12}$ alkyl group; wherein the deposition aid polymer has a degree of substitution, $DS_{(II)}$, of formula (II) moieties of 0.01 to 0.2 and a degree of substitution, $DS_{(III)}$, of formula (III) moieties of >0 to <0.02; and wherein the deposition aid polymer enhances the deposition of the dermatologically acceptable oil from the hair care formulation onto the mammalian hair relative to an otherwise identical formulation without the deposition aid polymer.

Unless otherwise indicated, ratios, percentages, parts, and the like are by weight.

As used herein, unless otherwise indicated, the phrase "molecular weight" or Mw refers to the weight average molecular weight as measured in a conventional manner with gel permeation chromatography (GPC) and conventional standards, such as polyethylene glycol standards. GPC techniques are discussed in detail in Modern Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons, or equivalently, g/mol.

The term "dermatologically acceptable" as used herein and in the appended refers to ingredients that are typically used for topical application to the skin, and is intended to underscore that materials that are toxic when present in the amounts typically found in skin care compositions are not contemplated as part of the present invention.

Preferably, the hair care formulation of the present invention is selected from the group consisting of a shampoo and a conditioning shampoo.

Preferably, the hair care formulation of the present invention, comprises: a dermatologically acceptable vehicle (preferably, wherein the hair care formulation comprises 35 to 98.89 wt % (preferably, 50 to 98.25 wt %; more preferably, 60 to 96.3 wt %; most preferably, 75 to 92.75 wt %), based on weight of the hair care formulation, of the dermatologically acceptable vehicle); a hair cleaning surfactant (preferably, wherein the hair care formulation comprises 1 to 50 wt % (preferably, 1.5 to 30 wt %; more preferably, 2.5 to 25 wt %; most preferably, 5 to 15 wt %), based on weight of the hair care formulation, of the hair cleaning surfactant); a dermatologically acceptable oil (preferably, wherein the hair care formulation comprises 0.01 to 10 wt % (preferably, 0.1 to 7.5 wt %; more preferably, 1 to 6 wt %; most preferably, 2 to 5 wt %), based on weight of the hair care formulation, of the dermatologically acceptable oil); and a deposition aid polymer (preferably, wherein the hair care formulation comprises 0.1 to 5 wt % (preferably, 0.15 to 3 wt %; more preferably, 0.2 to 1.5 wt %; most preferably, 0.25 to 0.75 wt %), based on weight of the hair care formulation, of the deposition aid polymer), wherein the deposition aid polymer is a cationic dextran polymer, comprising a dextran base polymer functionalized with quaternary ammonium groups; wherein the dextran base polymer has a weight average molecular weight of 50,000 to 3,000,000 Daltons; wherein the quaternary ammonium groups include (i) a quaternary ammonium group of formula (II) bound to a pendent oxygen on the dextran base polymer and (ii) a quaternary ammonium group of formula (III) bound to a pendent oxygen on the dextran base polymer (II)

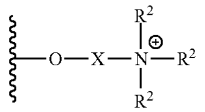

(III)

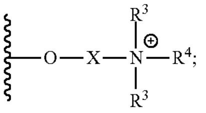

wherein

is a pendent oxygen on the dextran base polymer; wherein X is a divalent linking group; wherein each $R^2$ is independently selected from a $C_{1-4}$ alkyl group; wherein each $R^3$ is independently selected from a $C_{1-4}$ alkyl group; and wherein each $R^4$ is independently selected from a linear or branched $C_{12}$ alkyl group; wherein the deposition aid polymer has a degree of substitution, $DS_{(II)}$, of formula (II) moieties of 0.01 to 0.2 (preferably, 0.1 to 0.15) and a degree of substitution, $DS_{(III)}$, of formula (III) moieties of >0 to <0.02 (preferably, 0.0025 to 0.0049; more preferably, 0.003 to 0.0045; most preferably, 0.0035 to 0.004) (preferably, wherein the deposition aid polymer enhances the deposition of the dermatologically acceptable oil from the hair care formulation onto the mammalian hair relative to an otherwise identical formulation without the deposition aid polymer).

Preferably, the hair care formulation of the present invention is a liquid formulation. More preferably, the hair care formulation of the present invention is an aqueous liquid formulation.

Preferably, the hair care formulation of the present invention, comprises 35 to 98.89 wt % (preferably, 50 to 98.25 wt %; more preferably, 60 to 96.3 wt %; most preferably, 75 to 92.75 wt %), based on weight of the hair care formulation, of a dermatologically acceptable vehicle. More preferably, the hair care formulation of the present invention, comprises: 35 to 98.89 wt % (preferably, 50 to 98.25 wt %; more preferably, 60 to 96.3 wt %; most preferably, 75 to 92.75 wt %), based on weight of the hair care formulation, of a dermatologically acceptable vehicle; wherein the dermatologically acceptable vehicle comprises water. Yet more preferably, the hair care formulation of the present invention, comprises: 35 to 98.89 wt % (preferably, 50 to 98.25 wt %; more preferably, 60 to 96.3 wt %; most preferably, 75 to 92.75 wt %), based on weight of the hair care formulation, of a dermatologically acceptable vehicle; wherein the dermatologically acceptable vehicle is selected from the group consisting of water and an aqueous $C_{1-4}$ alcohol mixture. Most preferably, the hair care formulation of the present invention, comprises: 35 to 98.89 wt % (preferably, 50 to 98.25 wt %; more preferably, 60 to 96.3 wt %; most preferably, 75 to 92.75 wt %), based on weight of the hair care formulation, of a dermatologically acceptable vehicle; wherein the dermatologically acceptable vehicle is water.

Preferably, the water used in the hair care formulation of the present invention is at least one of distilled water and deionized water. More preferably, the water used in the hair care formulation of the present invention is distilled and deionized.

Preferably, the hair care formulation of the present invention comprises 1 to 50 wt % (preferably, 1.5 to 30 wt %; more preferably, 2.5 to 25 wt %; most preferably, 5 to 15 wt %), based on weight of the hair care formulation, of a hair cleaning surfactant. More preferably, the hair care formulation of the present invention comprises 1 to 50 wt % (preferably, 1.5 to 30 wt %; more preferably, 2.5 to 25 wt %; most preferably, 5 to 15 wt %), based on weight of the hair care formulation, of a hair cleaning surfactant; wherein the hair care cleaning surfactant is selected from the group consisting of alkyl polyglucosides (e.g., lauryl glucoside, coco-glucoside, decyl glucoside), glycinates (e.g., sodium cocoyl glycinate); betaines (e.g., alkyl betaines such as cetyl betaine and amido betaines such as cocamidopropyl betaine); taurates (e.g., sodium methyl cocoyl taurate); glutamates (e.g., sodium cocoyl glutamate); sarcosinates (e.g., sodium lauroyl sarcosinate); isethionates (e.g., sodium cocoyl isethionate, sodium lauroyl methyl isethionate); sulfoacetates (e.g., sodium lauryl sulfoacetate); alaninates (e.g., sodium cocoyl alaninate); amphoacetates (e.g., sodium cocoamphoacetate); sulfates (e.g., sodium lauryl ether sulfate (SLES)); sulfonates (e.g., sodium $C_{14-16}$ olefin sulfonate); succinates (e.g., disodium lauryl sulfosuccinate); fatty alkanolamides (e.g., cocamide monoethanolamine, cocamide diethanolamine, soyamide diethanolamine, lauramide diethanolamine, oleamide monoisopropanolamine, stearamide monoethanolamine, myristamide monoethanolamine, lauramide monoethanolamine, capramide diethanolamine, ricinoleamide diethanolamine, myristamide diethanolamine, stearamide diethanolamine, oleylamide diethanolamine, tallowamide diethanolamine, lauramide monoisopropanolamine, tallowamide monoethanolamine, isostearamide diethanolamine, isostearamide monoethanolamine); sophorolipids; alkyl polypentosides and mixtures thereof. Still more preferably, the hair care formulation of the present invention comprises t to 50 wt % (preferably, 1.5 to 30 wt %; more preferably, 2.5 to 25 wt %; most preferably, 5 to 15 wt %), based on weight of the hair care formulation, of a hair cleaning surfactant; wherein the hair cleaning surfactant includes a sodium lauryl ether sulfate. Most preferably, the hair care formulation of the present invention comprises 1 to 50 wt % (preferably, 1.5 to 30 wt %; more preferably, 2.5 to 25 wt %; most preferably, 5 to 15 wt %), based on weight of the hair care formulation, of a hair cleaning surfactant; wherein the hair care cleaning surfactant comprises a mixture of a betaine (preferably, cocamidopropyl betaine); a fatty alkanolamide (preferably, cocamide monoethanolamine); and a sodium lauryl ether sulfate.

Preferably, the hair care formulation of the present invention, comprises 0.01 to 10 wt % (preferably, 0.1 to 7.5 wt %; more preferably, 1 to 6 wt %; most preferably, 2 to 5 wt %), based on weight of the hair care formulation, of the dermatologically acceptable oil. More preferably, the hair care formulation of the present invention, comprises: 0.01 to 10 wt % (preferably, 0.1 to 7.5 wt %; more preferably, 1 to 6 wt %; most preferably, 2 to 5 wt %), based on weight of the hair care formulation, of the dermatologically acceptable oil; wherein the dermatologically acceptable oil is selected from the group consisting of hydrocarbon oils (e.g., mineral oil, petroleum jelly, polyisobutene, hydrogenated polyisobutene, hydrogenated polydecene, polyisohexadecane); natural oils (e.g., caprylic and capric triglyceride, sunflower oil, soybean oil, coconut oil, argan oil, olive oil, almond oil); fragrance oils (e.g., limonene, linalool, citronellol, benzyl alcohol) and mixtures thereof. Still more preferably, the hair care formulation of the present invention, comprises: 0.01 to 10 wt % (preferably, 0.1 to 7.5 wt %; more preferably, 1 to 6 wt %; most preferably, 2 to 5 wt %), based on weight of the hair care formulation, of the dermatologically acceptable oil; wherein the dermatologically acceptable oil includes a natural oil (e.g., caprylic and capric triglyceride, sunflower oil, soybean oil, coconut oil, argan oil, olive oil, almond oil). Yet more preferably, the hair care formulation of the present invention, comprises: 0.01 to 10 wt % (preferably, 0.1 to 7.5 wt %; more preferably, 1 to 6 wt %; most preferably, 2 to 5 wt %), based on weight of the hair care formulation, of a dermatologically acceptable oil; wherein the dermatologically acceptable oil includes coconut oil. Most preferably, the hair care formulation of the present invention, comprises: 0.01 to 10 wt % (preferably, 0.1 to 7.5 wt %; more preferably, 1 to 6 wt %; most preferably, 2 to 5 wt %), based on weight of the hair care formulation, of a dermatologically acceptable oil; wherein the dermatologically acceptable oil is coconut oil.

Preferably, the hair care formulation of the present invention, comprises: 0.1 to 5 wt % (preferably, 0.15 to 3 wt %; more preferably, 0.2 to 1.5 wt %; most preferably, 0.25 to 0.75 wt %), based on weight of the hair care formulation, of the deposition aid polymer; wherein the deposition aid polymer is a cationic dextran polymer, comprising a dextran base polymer functionalized with quaternary ammonium groups; wherein the dextran base polymer has a weight average molecular weight of 50,000 to 3,000,000 Daltons; wherein the quaternary ammonium groups include (i) a quaternary ammonium group of formula (II) bound to a pendent oxygen on the dextran base polymer; and (ii) a quaternary ammonium group of formula (III) bound to a pendent oxygen on the dextran base polymer.

Preferably, the dextran base polymer has a weight average molecular weight of 50,000 to 3,000,000 Daltons (preferably, 100,000 to 2,000,000 Daltons; more preferably, 125,000 to 1,000,000 Daltons; still more preferably, 130,000 to 650,000 Daltons; most preferably, 140,000 to 500,000 Daltons). More preferably, the dextran base polymer has a weight average molecular weight of (preferably, 100,000 to 2,000,000 Daltons; more preferably, 125,000 to 1,000,000 Daltons; still more preferably, 130,000 to 650,000 Daltons; most preferably, 140,000 to 500,000 Daltons); and the dextran base polymer is a branched chain dextran base polymer comprising a plurality of glucose structural units; wherein 90 to 98 mol % (preferably, 92.5 to 97.5 mol %; more preferably, 93 to 97 mol %; most preferably, 94 to 96 mol %) of the glucose structural units are connected by α-1,6 linkages and 2 to 10 mol % (preferably, 2.5 to 7.5 mol %; more preferably, 3 to 7 mol %; most preferably, 4 to 6 mol %) of the glucose structural units are connected by α-1,2 linkages, α-1,3 linkages and/or α-1,4 linkages. Most preferably, the dextran base polymer has a weight average molecular weight of (preferably, 100,000 to 2,000,000 Daltons; more preferably, 125,000 to 1,000,000 Daltons; still more preferably, 130,000 to 650,000 Daltons; most preferably, 140,000 to 500,000 Daltons); and the dextran base polymer is a branched chain dextran polymer comprising a plurality of glucose structural units; wherein 90 to 98 mol % (preferably, 92.5 to 97.5 mol %; more preferably, 93 to 97 mol %; most preferably, 94 to 96 mol %) of the glucose structural units are connected by α-D-1,6 linkages and 2 to 10 mol % (preferably, 2.5 to 7.5 mol %; more preferably, 3 to 7 mol %; most preferably, 4 to 6 mol %) of the glucose structural units are connected by α-1,3 linkages according to formula I (I)

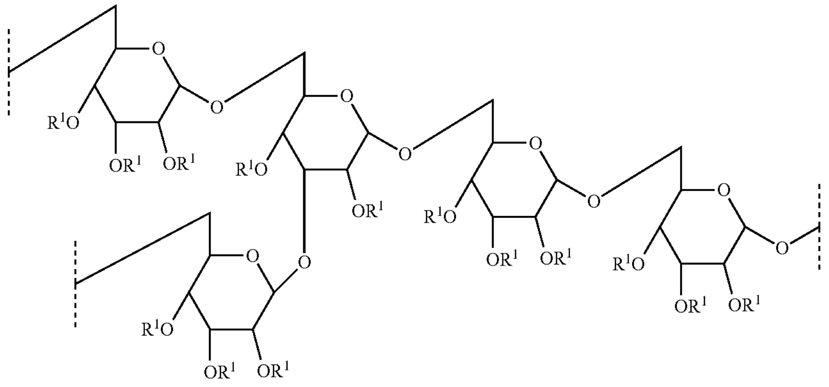

wherein $R^1$ is selected from a hydrogen, a $C_{1-4}$ alkyl group and a hydroxy $C_{1-4}$ alkyl group; and wherein the average branch off the dextran polymer backbone is 1 to 3 anhydroglucose units.

Preferably, the dextran base polymer contains less than 0.01 wt %, based on weight of the dextran base polymer, of alternan. More preferably, the dextran base polymer contains less than 0.001 wt %, based on weight of the dextran base polymer, of alternan. Most preferably, the dextran base polymer contains less than the detectable limit of alternan.

Preferably, <0.1 mol % (preferably, <0.01 mol %; more preferably, <0.001 mol %; most preferably, <detectable limit), of the glucose structural units in the dextran base polymer are connected by β-1,4 linkages.

Preferably, <0.1 mol % (preferably, <0.01 mol %; more preferably, <0.001 mol %; most preferably, <detectable limit), of the glucose structural units in the dextran base polymer are connected by β-1,3 linkages.

Preferably, the hair care formulation of the present invention comprises 0.1 to 5 wt % (preferably, 0.15 to 3 wt %; more preferably, 0.2 to 1.5 wt %; most preferably, 0.25 to 0.75 wt %), based on weight of the hair care formulation, of the deposition aid polymer; wherein the deposition aid polymer is a cationic dextran polymer, comprising a dextran base polymer functionalized with quaternary ammonium groups; wherein the quaternary ammonium groups include (i) a quaternary ammonium group of formula (II) bound to a pendent oxygen on the dextran base polymer and (ii) a quaternary ammonium group of formula (III) bound to a pendant oxygen on the dextran base polymer (II)

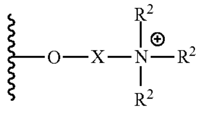

-continued (III)

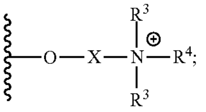

wherein

is a pendent oxygen on the dextran base polymer; wherein X is a divalent linking group; wherein X is a divalent linking group (preferably, wherein X is selected from divalent alkyl groups, which may optionally be substituted with a hydroxy group, an alkoxy group and/or an ether group; more preferably, wherein X is a $-CH_2CH(OR^5)CH_2-$ group, where $R^5$ is selected from the group consisting of a hydrogen and a linear or branched $C_{1-4}$ alkyl group; most preferably, wherein X is a $-CH_2CH(OH)CH_2-$ group); wherein each $R^2$ is independently selected from a linear or branched $C_{1-4}$ alkyl group (preferably, a linear or branched $C_{1-3}$ alkyl group; more preferably, a $C_{1-2}$ alkyl group; most preferably, a methyl group); wherein each $R^3$ is independently selected from a linear or branched $C_{1-4}$ alkyl group (preferably, a linear or branched $C_{1-3}$ alkyl group; more preferably, a $C_{1-2}$ alkyl group; most preferably, a methyl group); and wherein each $R^4$ is independently selected from a linear or branched $C_{12}$ alkyl group (preferably, a linear $C_{12}$ alkyl group); wherein the deposition aid polymer has a degree of substitution, $DS_{(II)}$, of formula (II) moieties of 0.01 to 0.2 (preferably, 0.1 to 0.15) and a degree of substitution, $DS_{(III)}$, of formula (III) moieties of >0 to <0.02 (preferably, 0.0025 to 0.0049; more preferably, 0.003 to 0.0045; most preferably, 0.0035 to 0.004). More preferably, the hair care formulation of the present invention comprises 0.1 to 5 wt % (preferably, 0.15 to 3 wt %; more preferably, 0.2 to 1.5 wt %; most preferably, 0.25 to 0.75 wt %), based on weight of the hair care formulation, of the deposition aid polymer; wherein the deposition aid polymer is a cationic dextran polymer, comprising a dextran base polymer functionalized with quaternary ammonium groups; wherein the quaternary ammonium groups include (i) a quaternary ammonium group of formula (IIa) bound to a pendent oxygen on the dextran base polymer and (ii) a quaternary ammonium group of formula (IIIa) bound to a pendant oxygen on the dextran base polymer (IIa)

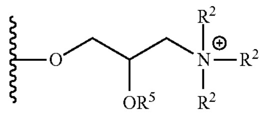

(IIIa)

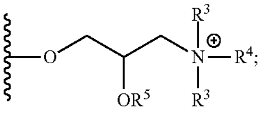

wherein

is a pendent oxygen on the dextran base polymer; wherein each $R^2$ is independently selected from a linear or branched $C_{1-4}$ alkyl group (preferably, a $C_{1-3}$ alkyl group; more preferably, a $C_{1-2}$ alkyl group; most preferably, a methyl group); wherein each $R^3$ is independently selected from a linear or branched $C_{1-4}$ alkyl group (preferably, a $C_{1-3}$ alkyl group; more preferably, a $C_{1-2}$ alkyl group; most preferably, a methyl group); wherein each $R^4$ is independently selected from a linear or branched $C_{12}$ alkyl group (preferably, a linear $C_{12}$ alkyl group); and wherein each $R^5$ is independently selected from the group consisting of a hydrogen and a linear or branched $C_{1-4}$ alkyl group (preferably, a hydrogen); wherein the deposition aid polymer has a degree of substitution, $DS_{(II)}$, of formula (II) moieties of 0.01 to 0.2 (preferably, 0.1 to 0.15) and a degree of substitution, $DS_{(III)}$, of formula (III) moieties of >0 to <0.02 (preferably, 0.0025 to 0.0049; more preferably, 0.003 to 0.0045; most preferably, 0.0035 to 0.004). Most preferably, the hair care formulation of the present invention comprises 0.1 to 5 wt % (preferably, 0.15 to 3 wt %; more preferably, 0.2 to 1.5 wt %; most preferably, 0.25 to 0.75 wt %), based on weight of the hair care formulation, of the deposition aid polymer; wherein the deposition aid polymer is a cationic dextran polymer, comprising a dextran base polymer functionalized with quaternary ammonium groups; wherein the quaternary ammonium groups include (i) a quaternary ammonium group of formula (IIa) bound to a pendent oxygen on dextran the polymer; and (ii) a quaternary ammonium group of formula (IIIa) bound to a pendent oxygen on dextran the polymer; wherein each $R^2$ is a methyl group; wherein each $R^3$ is a methyl group; wherein each $R^4$ is a linear $C_{12}$ alkyl group; and wherein each $R^5$ is a hydrogen; wherein the deposition aid polymer has a degree of substitution, $DS_{(II)}$, of formula (II) moieties of 0.01 to 0.2 (preferably, 0.1 to 0.15) and a degree of substitution, $DS_{(III)}$, of formula (III) moieties of >0 to <0.02 (preferably, 0.0025 to 0.0049; more preferably, 0.003 to 0.0045; most preferably, 0.0035 to 0.004).

Preferably, the deposition aid polymer has a Kjeldahl nitrogen content, TKN, of 0.5 to 2 wt % (preferably, 0.6 to 1.5 wt %; more preferably, 0.65 to 1 wt %; most preferably, 0.7 to 0.8 wt %) measured using a Buchi KjelMaster K-375 automated analyzer, corrected for volatiles and ash measured as described in ASTM method D-2364.

Preferably, 70 to 98 wt % (preferably, 75 to 97 wt %; more preferably, 85 to 96 wt %; most preferably, 90 to 95 wt %) of the quaternary ammonium groups on the deposition aid polymer are of formula (II) (preferably, wherein the quaternary ammonium groups of formula (II) are of formula (IIa)) and 2 to 30 wt % (preferably, 3 to 25 wt %; more preferably, 4 to 15 wt %; most preferably, 5 to 10 wt %) of the quaternary ammonium groups on the deposition aid polymer of formula (III) (preferably, wherein the quaternary ammonium groups of formula (III) are of formula (IIIa).

Preferably, the deposition aid polymer contains <0.001 meg/gram (preferably, <0.0001 meq/gram; more preferably, <0.00001 meq/gram; most preferably, <detectable limit) of aldehyde functionality.

Preferably, the deposition aid polymer contains <0.001 meq/gram (preferably, <0.0001 meq/gram; more preferably, <0.00001 meq/gram; most preferably, <detectable limit) of silicone containing functionality.

Preferably, the deposition aid polymer contains <0.1 mol % (preferably, 0 to <0.01 mol %; more preferably, 0 to <0.001 mol %; most preferably, 0 to <detectable limit) of structural units of a reactive siloxane, wherein the structural units of a reactive siloxane include Si—O moieties. More preferably, the deposition aid polymer contains <0.1 mol % (preferably, 0 to <0.01 mol %; more preferably, 0 to <0.001 mol %; most preferably, 0 to <detectable limit) of structural units of a reactive siloxane, wherein the structural units of a reactive siloxane include Si—O moieties; wherein the reactive siloxane is a polymer which may comprise one or more functional moieties selected from the group consisting of amino, amido, alkoxy, hydroxy, polyether, carboxy, hydride, mercapto, sulfate phosphate, and/or quaternary ammonium moieties—these moieties may be attached directly to the siloxane backbone through a bivalent alkylene radical, (i.e., pendant) or may be part of the backbone.

Preferably, the formulation for the care of damaged hair (preferably, mammalian hair; more preferably, human hair) of the present invention, optionally, further comprises at least one additional ingredient selected from the group consisting of an absorbent; an acid; an antidandruff agent; an anti-frizz agent; an antimicrobial agent/preservative (e.g., benzoic acid, sorbic acid, phenoxyethanol, methylisothiazolinone, ethylhexyl glycerin); an antioxidant (e.g., butylated hydroxytoluene); an antistatic agent; a bleaching agent; a bioactive agent; a chelating agent (e.g., tetrasodium ethylene diamine tetraacetic acid); a colorant; a conditioning agent (e.g., guar hydroxypropyltrimonium chloride, PQ-10, PQ-7); an emulsifying agent; a foaming agent; a fragrance; a hair styling agent; a hair waving/straightening agent; a humectant (e.g., glycerin, sorbitol, monoglycerides, lecithins, glycolipids, fatty alcohols, fatty acids, polysaccharides, sorbitan esters, polysorbates (e.g., Polysorbate 20, Polysorbate 40, Polysorbate 60, and Polysorbate 80), diols (e.g., propylene glycol), diol analogs, triols, triol analogs, cationic polymeric polyols); a lubricating agent; a natural ingredient; an opacifier; a pearlizing agent; a pH adjusting agent; a pigment; a plant extract; a preservative (e.g., benzoic acid, sorbic acid, phenoxyethanol, methylisothiazolinone); a protein/amino acid; a salt; a sensory modifier; a slip agent; a soap; a sunscreen additive; a thickener (e.g., PEG-150 pentaerythrityl tetrastearate); a vitamin and a wax. More preferably, the hare care formulation of the present invention, optionally, further comprises at least one additional ingredient selected from the group consisting of an antimicrobial agent/preservative (e.g., benzoic acid, sorbic acid, phenoxyethanol, methylisothiazolinone, ethylhexyl glycerin); a thickener (e.g., PEG-150 pentaerythrityl tetrastearate); a chelating agent (e.g., tetrasodium ethylene diamine tetraacetic acid) and a salt (sodium chloride). Most preferably, the hair care formulation of the present invention, optionally, further comprises at least one additional ingredient selected from the group consisting of a mixture of phenoxyethanol and methylisothiazolinone; a mixture of phenoxyethanol and ethylhexyl glycerin; PEG-150 pentaerythrityl tetrastearate; tetrasodium ethylene diamine tetraacetic acid and sodium chloride Preferably, the hair care formulation further comprises a thickener. More preferably, the hair care formulation further comprises a thickener, wherein the thickener is selected to increase the viscosity of the hair care formulation, preferably without substantially modifying the other properties of the hair care formulation. Preferably, the hair care formulation further comprises a thickener, wherein the thickener is selected to increase the viscosity of the hair care formulation, preferably without substantially modifying the other properties of the hair care formulation and wherein the thickener accounts for 0 to 5.0 wt % (preferably, 0.1 to 5.0 wt %; more preferably, 0.2 to 2.5 wt %; most preferably, 0.5 to 2.0 wt %), based on weight of the hair care formulation.

Preferably, the hair care formulation of the present invention further comprises an antimicrobial agent/preservative. More preferably, the hair care formulation of the present invention further comprises an antimicrobial/preservative, wherein the antimicrobial/preservative is selected from the group consisting of phenoxyethanol, benzoic acid, benzyl alcohol, sodium benzoate, DMDM hydantoin, 2-ethylhexyl glyceryl ether, isothiazolinone (e.g., methylchloroisothiazolinone, methylisothiazolinone) and mixtures thereof. Still more preferably, the hair care formulation of the present invention, further comprises an antimicrobial/preservative, wherein the antimicrobial/preservative is a mixture of phenoxyethanol and an isothiazolinone (more preferably, wherein the antimicrobial/preservative is a mixture of phenoxyethanol and methylisothiazolinone).

Preferably, the hair care formulation of the present invention optionally further comprises a pH adjusting agent. More preferably, the hair care formulation of the present invention, further comprises a pH adjusting agent, wherein the hair care formulation has a pH of 4 to 9 (preferably, 4.25 to 8; more preferably, 4.5 to 7; most preferably, 5 to 6).

Preferably, the pH adjusting agent is selected from the group consisting of at least one of citric acid, lactic acid, hydrochloric acid, aminoethyl propanediol, triethanolamine, monoethanolamine, sodium hydroxide, potassium hydroxide, amino-2-methyl-1-propanol. More preferably, the pH adjusting agent is selected from the group consisting of at least one of citric acid, lactic acid, sodium hydroxide, potassium hydroxide, triethanolamine, amino-2-methyl-1-propanol. Still more preferably, the pH adjusting agent includes citric acid. Most preferably, the pH adjusting agent is citric acid.

Preferably, the hair care formulation of the present invention contains <0.1 wt % (preferably, <0.001 wt %; more preferably, <0.0001 wt %; most preferably, <detectable limit), based on weight of the hair conditioner formulation, of silicone (e.g., polydimethylsiloxane, dimethicone, cyclodimethicone).

Preferably, the method of depositing oil on to mammalian hair (preferably, human hair) of the present invention, comprises: selecting a hair care formulation of the present invention and applying the hair care formulation to the mammalian hair (preferably, human hair)(preferably, wherein the deposition aid polymer enhances the deposition of the dermatologically acceptable oil from the hair care formulation onto the mammalian hair relative to an otherwise identical formulation without the deposition aid polymer). More preferably, the method of depositing oil on to mammalian hair (preferably, human hair) of the present invention, further comprises: rinsing the hair care formulation from the mammalian hair (preferably, human hair) with a rinse water. Most preferably, the method of depositing oil on to mammalian hair (preferably, human hair) of the present invention, comprises: selecting a hair care formulation of the present invention; applying the hair care formulation to the mammalian hair (preferably, human hair); and rinsing the hair care formulation from the mammalian hair (preferably, human hair); wherein the deposition aid polymer enhances the deposition of the dermatologically acceptable oil from the hair care formulation onto the mammalian hair relative to an otherwise identical formulation without the deposition aid polymer.

Some embodiments of the present invention will now be described in detail in the following Examples.

Synthesis S1: Synthesis of Cationic Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with dextran polymer (30.1 g; Sigma-Aldrich product D4876) and deionized water (69.8 g). The weight average molecular weight of the dextran polymer was 100,000 to 200,000 Daltons. The addition funnel was charged with a 40% aqueous solution of 3-chloro-2-hydroxypropyl-lauryl-dimethylammonium chloride (1.6 g; QUAB® 342 available from SKW QUAB Chemicals). While the flask contents were stirring, the apparatus was purged with nitrogen to displace any oxygen entrained in the system for one hour. The nitrogen flow rate was about 1 bubble per second.

Using a plastic syringe, a 25% aqueous sodium hydroxide solution (6.4 g) was added over a period of a couple minutes to the flask contents with stirring under nitrogen. The flask contents were then allowed to stir under nitrogen for one hour. The contents of the addition funnel were then charged to the flask contents dropwise over a few minutes under nitrogen with continued stirring. After the contents of the addition funnel were transferred to the flask contents, the mixture was allowed to stir for 20 minutes. Then heat was applied to the flask contents with a heating mantle controlled using the J-KEM controller set at 70 °C. The flask contents were heated to and maintained at 70 °C for 30 minutes.

Then a 70% aqueous solution of 2,3-epoxypropyltrimethylammonium chloride (16.3 g; QUAB® 151 available from SKW QUAB Chemicals) was added dropwise to the flask contents over a period of one hour while maintaining the J-KEM controller set at 70 °C. The flask contents were then cooled in an ice water bath while maintaining a positive nitrogen pressure in the flask. When the flask contents reached room temperature, glacial acetic acid (1.94 g) was added to the flask contents. The flask contents were then stirred for 10 minutes under nitrogen. The product solution was used without further purification. The product polymer was characterized by nuclear magnetic resonance (1H NMR) for structural analysis to determine the degree of substitution, $DS_{(II)}$, of trimethyl ammonium moieties and, $DS_{(III)}$, of dimethyldodecyl ammonium moieties reported in TABLE 2.

Syntheses S2-S3: Synthesis of Cationic Dextran Polymer

In Syntheses S2-S3, cationic dextran polymers were prepared substantially as described in Synthesis S1 but with varying reagent feeds as noted in TABLE 1. The degree of substitution, $DS_{(II)}$, of the QUAB® 151 and, $DS_{(III)}$, of the QUAB® 342 in the product cationic dextran polymers measured by 1H NMR is reported in TABLE 2. The calculated total Kjeldahl nitrogen, TKN, in the product cationic dextran polymers based on the DS values is also reported in TABLE 2.

TABLE 1

| Ex. | Dextran (g) | Water (g) | NaOH (g) | QUAB ® 151 (g) | Quat 188[1] | QUAB ® 342 (g) |
|---|---|---|---|---|---|---|
| S1 | 30.1 | 69.8 | 1.6 | 16.3 | 0 | 1.6 |
| S2 | 21.6 | 35.8 | 14.6 | 0 | 14.2 | 15.8 |
| S3 | 40.2 | 89.6 | 6.4 | 20.9 | 0 | 0 |

[1]A 65% aqueous solution of N-(3-chloro-2-hydroxypropyl)trimethylammonium chloride available from The Dow Chemical Company.

TABLE 2

| Ex. | Trimethyl ammonium, DS | Dimethyl dodecyl ammonium, DS | TKN |
|---|---|---|---|
| S1 | 0.114 | 0.0038 | 0.745 |
| S2 | 0.077 | 0.0200 | 0.796 |
| S3 | 0.210 | 0 | 1.751 |

Comparative Examples CF1-CF2 and Example F1: Shampoo Formulations

A shampoo formulation was prepared in each of Comparative Examples CF1-CF2 and Example F1 using the generic shampoo formulation noted in TABLE 3.

TABLE 3

| Ingredient INCI name | CF1 wt % | CF2 wt % | CF3 wt % | CF4 wt % | F1 wt % |
|---|---|---|---|---|---|
| Deionized water | | | q.s. 100 | | |
| 28 wt % aq. soln. Sodium Lauryl Ether Sulfate[1] | 32.1 | 32.1 | 32.1 | 32.1 | 32.1 |
| Unmodified Dextran[2] | — | — | 0.3 | — | — |
| Example S1 (30% polymer) | — | — | — | — | 1 |
| Example S2 (27% polymer) | 1.1 | — | — | — | — |
| Example S3 (27% polymer) | — | 1.1 | — | — | — |
| Tetrasodium EDTA[3] | 0.2 | 0.2 | 0.2 | 0.2 | 0.2 |
| Cocamide MEA[4] | 1.0 | 1.0 | 1.0 | 1.0 | 1.0 |
| 30 wt % aq. soln. Cocamidopropyl Betaine[5] | 6.0 | 6.0 | 6.0 | 6.0 | 6.0 |
| Phenoxyethanol and Methylisothiazolinone[6] | 0.5 | 0.5 | 0.5 | 0.5 | 0.5 |
| Coconut oil[7] | 4.0 | 4.0 | 4.0 | 4.0 | 4.0 |
| Sodium Chloride | | | q.s. Viscosity 10,000-15,000 cP | | |
| Citric Acid | | | q.s. pH 5-6 | | |

TABLE 3-continued

| Ingredient INCI name | CF1 wt % | CF2 wt % | CF3 wt % | CF4 wt % | F1 wt % |
|---|---|---|---|---|---|

[1]available from Stepan Company under tradename Steol ® CS-330
[2]Sigma-Aldrich catalog number D4876
[3]available from The Dow Chemical Company under tradename Versene ™ 220
[4]available from Croda Inc. under tradename Incromide CMEA
[5]available from Stepan Company under tradename Amphosol CA
[6]available from The Dow Chemical Company under tradename Neolone ™ PE
[7]available from Marico Parachute brand

Coconut Oil Deposition Analysis

The coconut oil deposition on hair from the shampoo formulations prepared according to Comparative Examples CF1-CF7 and Example F1 was quantified using GC-MS.

Hair tresses (2 g, European Virgin Brown available from International Hair Importers) were initially washed in a 9 wt % sodium lauryl sulfate (SLS) solution (0.4 g) by massaging into the tress for 30 seconds and then rinsed with water flowing at 0.4 L/min for one minute. Following the initial wash step, the hair tresses were then washed with a shampoo formulation of Comparative Examples CF1-CF4 and Example F1 by applying 0.8 g of the shampoo formulation to the hair tress and massaging in for 30 seconds on each side and then rinsing with water flowing at 0.4 L/min for 15 seconds on each side. The tresses were then allowed to air dry prior to deposition analysis.

The treated hair samples (1 g) were extracted with hexanes (20 mL) on a shaker overnight (~12 hours). A 1 M KOH in methanol solution was prepared. An extract from each hair sample (4 mL) was mixed in a vial with 1 M KOH (0.4 mL) and octadecane (0.2 mL, 100 ppm in hexanes). The vials were then placed on a shaker for 1 hour. The vials were then placed in a hood for 5 minutes. A 3 mL sample from the top layer in each vial was mixed with 3 mL of saturated aqueous NaCl solution in a separate vial, which was then placed on a shaker for 5 minutes. The vials were then allowed to settle for 5 minutes before taking a 1 ml sample from the top layer and injecting into a GC-MS for analysis. The instrument parameters used are provided in TABLE 4. The results are provided in TABLE 5.

TABLE 4

| | |
|---|---|
| Instrument | Agilent 7890A GC/5977A MS |
| Data system | Masshunter |
| Column: | Agilent DB-Wax, 30 m × 0.25 mm, 0.25 μm film |
| Carrier flow rate | 1.2 mL/min Helium column connected to a split plate restrictor capillary (5.0 m × 0.180 mm × 0 μm) |
| Inlet | Temperature: 250 °C<br>Injection 1 μL<br>Split ratio: 10:1 |
| Oven Temperature Programming: | 100 °C for 2 min, ramped at 10 °C/min to 250 °C, and held for 5 min. |
| MS transfer line temperature | 250 °C |
| SIM Parameters: | Group 1: 5-11 min; octadecane (as an internal standard): $t_R$, 9.93 min; ion 57 |

TABLE 4-continued

| |
|---|
| (quantifier) and 71 (qualifier) Group 2: 11 min; $C_{14}$ acid methyl ester: $t_R$, 12.15 min; ion 74 (quantifier) and 87 (qualifier) |

TABLE 5

| Shampoo Formulation | TKN % | Coconut oil deposition (wt %) |
|---|---|---|
| Comparative Example CF1 | 0.796 | 0.17 |
| Comparative Example CF2 | 1.751 | 0.37 |
| Comparative Example CF3 | 0 | 0.14 |
| Comparative Example CF4 | 0 | 0.12 |
| Example F1 | 0.745 | 1.11 |

We claim:

1. A hair care formulation, comprising:

a dermatologically acceptable vehicle;

a hair cleaning surfactant;

a dermatologically acceptable oil; and a deposition aid polymer, wherein the deposition aid polymer is a cationic dextran polymer, comprising a dextran base polymer functionalized with quaternary ammonium groups; wherein the dextran base polymer has a weight average molecular weight of 50,000 to 3,000,000 Daltons; wherein the quaternary ammonium groups include (i) a quaternary ammonium group of formula (II) bound to a pendent oxygen on the dextran base polymer (II)

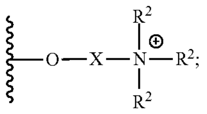

and (ii) a quaternary ammonium group of formula (III) bound to a pendent oxygen on the dextran base polymer (III)

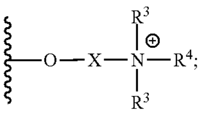

wherein

is a pendent oxygen on the dextran base polymer; wherein X is a divalent linking group; wherein each $R^2$ is independently selected from a $C_{1-4}$ alkyl group; wherein each $R^3$ is independently selected from a $C_{1-4}$ alkyl group; and wherein each $R^4$ is independently selected from a linear or branched $C_{12}$ alkyl group; wherein deposition aid polymer has a degree of substitution, $DS_{(II)}$, of formula (II) moieties of 0.01 to 0.2 and a degree of substitution, $DS_{(III)}$, of formula (III) moieties of >0 to <0.02.

2. The hair care formulation of claim 1, wherein the hair care formulation contains less than 0.1 wt %, based on weight of the hair care formulation, of silicon containing molecules.

3. The hair care formulation of claim 2, wherein the hair care formulation is selected from the group consisting of a shampoo and a conditioning shampoo.

4. The hair care formulation of claim 2, wherein the deposition aid polymer has a Kjeldahl nitrogen content corrected for ash and volatiles, TKN, of 0.5 to 2.0 wt %.

5. The hair care formulation of claim 4, wherein the dextran base polymer is a branched chain dextran polymer.

6. The hair care formulation of claim 5, wherein each $R^2$ and $R^3$ is a methyl group and wherein $R^4$ is a linear $C_{12}$ alkyl group.

7. The hair care formulation of claim 6, further comprising a chelating agent, a thickener and a preservative.

8. The hair care formulation of claim 7, wherein the hair care cleaning surfactant comprises a mixture of sodium lauryl ether sulfate, cocamide monoethanolamine and cocamidopropyl betaine; wherein the chelating agent comprises tetrasodium ethylenediaminetetraacetic acid; and wherein the thickener comprises PEG-150 pentaerythrityl tetrastearate.

9. A method of depositing oil on to mammalian hair, comprising:

selecting a hair care formulation according to claim 1;

applying the hair care formulation to mammalian hair;

wherein the deposition aid polymer enhances the deposition of the dermatologically acceptable oil from the hair care formulation onto the mammalian hair relative to an otherwise identical formulation without the deposition aid polymer.

* * * * *